United States Patent
Godfrey

(10) Patent No.: US 9,746,393 B2
(45) Date of Patent: Aug. 29, 2017

(54) FIBRE OPTIC SENSING

(71) Applicant: OPTASENSE HOLDINGS LIMITED, Farnborough, Hampshire (GB)

(72) Inventor: Alastair Godfrey, Farnborough (GB)

(73) Assignee: OPTASENSE HOLDINGS LIMITED (GB)

(*) Notice: Subject to any disclaimer, the term of this patent is extended or adjusted under 35 U.S.C. 154(b) by 182 days.

(21) Appl. No.: 14/410,851

(22) PCT Filed: Jun. 27, 2013

(86) PCT No.: PCT/GB2013/051701
§ 371 (c)(1),
(2) Date: Dec. 23, 2014

(87) PCT Pub. No.: WO2014/001807
PCT Pub. Date: Jan. 3, 2014

(65) Prior Publication Data
US 2015/0128706 A1    May 14, 2015

(30) Foreign Application Priority Data

Jun. 29, 2012 (GB) .................................. 1211561.4

(51) Int. Cl.
*G01N 29/09* (2006.01)
*G01D 5/353* (2006.01)
*G01M 11/08* (2006.01)

(52) U.S. Cl.
CPC ....... *G01M 11/088* (2013.01); *G01D 5/35358* (2013.01); *G01N 29/09* (2013.01); *G01N 2291/018* (2013.01)

(58) Field of Classification Search
CPC ................. G01M 11/088; G01N 29/09; G01N 2291/018
(Continued)

(56) References Cited

U.S. PATENT DOCUMENTS 3,941,927 A    3/1976   Russell
4,376,248 A *   3/1983   Giallorenzi ............ G01R 33/02
                                                                   250/227.19
(Continued)

FOREIGN PATENT DOCUMENTS

EP        0591848      4/1994
EP        1077360      2/2001
(Continued)

*Primary Examiner* — J M Saint Surin
(74) *Attorney, Agent, or Firm* — McDonnell Boehnen Hulbert & Berghoff LLP

(57) ABSTRACT

This application relates to methods and apparatus for fiber optic sensing which can provide information about the environment in which the fiber optic is deployed. In particular the application relates to fiber optic based sensing of the mechanical impedance of the environment. The method comprises using an interrogator (201) to interrogate an optical fiber (104) which is coupled to a first element (202; 802) which is responsive to electromagnetic fields. In use a varying electric current (I), which may be an alternating current, is applied so as to induce a varying force (F) on said first element. The optical radiation backscattered from within the optical fiber is analyzed to determine a measurement signal indicative of a variation in the backscattered radiation corresponding with said electric current applied. The first element may be a first conductor (202) and the varying current may be supplied to the first conductor, or to a second conductor (701). Alternatively the first element could be a magnetic element (802). By applying a variable force to the first element, and hence the optical fiber, the characteristics of the environment can be determined.

22 Claims, 4 Drawing Sheets

(58) Field of Classification Search
USPC .......................................................... 73/574
See application file for complete search history.

(56) References Cited

U.S. PATENT DOCUMENTS

| | | | | |
|---|---|---|---|---|
| 5,992,250 A * | 11/1999 | Kluth | ..................... | E21B 17/003 254/134.4 |
| 6,520,911 B1 * | 2/2003 | Wen | ..................... | A61B 5/0093 600/437 |
| 6,532,839 B1 * | 3/2003 | Kluth | ..................... | E21B 17/003 166/385 |
| 2001/0055462 A1 | 12/2001 | Seibel | | |
| 2003/0010500 A1 * | 1/2003 | Smith | ................. | E21B 47/0001 166/336 |
| 2004/0065444 A1 * | 4/2004 | Smith | ..................... | E21B 23/08 166/381 |
| 2009/0102474 A1 * | 4/2009 | Cranch | ................. | A01D 89/008 324/244.1 |
| 2011/0098931 A1 * | 4/2011 | Kosmala | ................. | E21B 47/00 702/12 |
| 2013/0154632 A1 * | 6/2013 | McEwen-King | .... | G02B 6/4401 324/244.1 |
| 2013/0197739 A1 * | 8/2013 | Gallagher | ............. | B64F 5/0045 701/31.5 |
| 2014/0174752 A1 * | 6/2014 | Sipila | ................. | E21B 47/0006 166/336 |

FOREIGN PATENT DOCUMENTS

| | | |
|---|---|---|
| EP | 1 496 369 | 4/2008 |
| GB | 2442745 | 4/2008 |
| JP | 01035284 | 2/1989 |
| JP | S64 35284 | 2/1989 |
| WO | WO 2012/028846 | 3/2012 |
| WO | WO 2012/089818 | 7/2012 |

* cited by examiner

FIBRE OPTIC SENSING

FIELD OF THE INVENTION

This application relates to fibre optic sensing, such as fibre optic distributed acoustic sensing, with detection/monitoring of the characteristics of the environment surrounding the fibre optic. In particular the application relates to apparatus and methods for fibre optic sensing that allow detection of the characteristics of a medium in contact with the sensing fibre optic cable, such as the mechanical or acoustic impedance of said medium.

BACKGROUND OF THE INVENTION

Fibre optic sensing is known for a variety of different applications. Fibre optic sensors typically operate by interrogating an optical fibre with optical radiation and analysing any radiation backscattered, either from deliberate point sensors within the fibre (e.g. Fibre Bragg gratings or the like) for from intrinsic scattering sites within the fibre itself, to determine various parameters such as strain, vibration or temperature.

One type of fibre optic sensing is fibre optic distributed acoustic sensing (DAS) wherein the optical fibre is interrogated to provide sensing of acoustic activity along its length. Typically one or more optical pulses are launched into the fibre and the radiation backscattered from within the fibre is detected, i.e. backscatter from intrinsic scattering sites inherent in the fibre rather deliberately introduced discrete reflectors. The detected backscattered radiation is analysed. The analysis effectively divides the optical fibre into a plurality of discrete sensing portions. Within each discrete sensing portion mechanical disturbances of the fibre, for instance due to incident acoustic waves, cause a variation in the properties of the radiation which is backscattered from that portion. This variation is detected and analysed and used to give a measure of the intensity of disturbance of the fibre at that sensing portion. GB2,442,745 describes one example of a DAS system. As the radiation which is detected any analysed is scattered from the intrinsic scattering sites in the fibre the scattering, and hence the sensing function, is distributed along the whole length of the fibre.

DAS has been proposed for a variety of different applications. For instance it has been proposed to use fibre optic DAS for perimeter security, using a sensing fibre optic deployed along the route of the perimeter of interest to monitor for acoustic signals associated with intruders. It has also been suggested to use fibre optic sensors for structural monitoring by embedding optical fibres within the medium of the structure to be monitored.

DAS thus relies on incident pressure waves/vibrations acting on the optical fibre so as to alter the characteristics of the backscatter from the fibre. The response of a DAS sensor to a given stimulus may however be dependent on the environment in which the optical fibre is deployed and the coupling of the optical fibre, which will generally be in some sort of fibre optic cable structure, to the surrounding environment.

In some applications it would be useful to determine some characteristics of the environment in which the optical fibre is deployed. Embodiments of the present invention therefore provide fibre optics sensors able to determine some characteristic of the environment in which the sensing fibre is deployed.

SUMMARY OF THE INVENTION

Thus according to the present invention there is provided a method of fibre optic sensing comprising: interrogating an optical fibre deployed in an area of interest with optical radiation wherein at least part of the optical fibre is mechanically coupled to at least a first element responsive, in use, to electromagnetic fields; applying a varying electric current so as to induce a varying force on said first element; and analysing optical radiation backscattered from within said optical fibre to determine a measurement signal indicative of any variation in the backscattered radiation corresponding with said electric current applied and analysing said measurement signal to determine a characteristic of the environment in which the optical fibre is deployed.

The method thus mechanically couples at least part of the optical fibre which is used for sensing to a first element which is, in use, responsive to electromagnetic fields. In other words the first element is configured such that an applied electric field and/or magnetic field may induce a force on the first element. The method therefore involves applying a varying current so as to induce a varying force on the first element. In particular the current applied may be an alternating current.

Inducing a varying force on the first element, which is mechanically coupled to the optical fibre, will result in at least some force also being applied to the optical fibre. This can result in a detectable change in the properties of optical radiation backscattered from the optical fibre. In essence the induced force provides a stimulus to the fibre which may be detected using the techniques of distributed acoustic sensing as described above to provide a measurement signal. The use of an alternating current to provide a varying force in effect provides a continuous acoustic type stimulus.

The degree of variation in properties of the backscattered radiation, and hence the detected measurement signal, will however be dependent on the environment in which the optical fibre is deployed and thus the measurement signals may be used to determine various characteristics about the environment as will be described in more detail later.

In one embodiment the first element may be a first conductor which, in use, carries an electric current. As will be understood by one skilled in the art a conductor in which a current is flowing will, in the presence of a magnetic field, experience a force dependent on the magnetic field and on the current flow. The method may therefore comprise generating, in use, an electric current in the first conductor in the presence of a magnetic field wherein the varying current is applied so as to create varying current flow in the first conductor and/or a varying magnetic field.

In some embodiments the varying current, e.g. alternating current, may be applied to the first conductor. The method therefore may comprise arranging the optical fibre and first conductor in a magnetic field in use, and applying the alternating current to the first conductor to induce the varying force on the first conductor. By applying the varying current to the first conductor is meant generating the varying current in the conductor.

In some embodiments substantially the main component of the magnetic field acting on the first conductor may be the ambient magnetic field in the vicinity of the fibre, for example the field resulting from the earth's magnetic field. In other words the optical fibre and first conductor may be deployed in a location of interest such that any magnetic fields acting on the first conductor in use arise from the location of interest itself (rather than any element specifically deployed to generate a magnetic field).

In some embodiments the method may rely mainly on the earth's ambient magnetic field at the location of the sensing fibre and first conductor. It has been found that applying an alternating current to a conductor coupled to an optical fibre can produce a detectable signal in the backscatter from the optical fibre, i.e. a detectable measurement signal, in the presence of just the earth's ambient magnetic field. The method may therefore comprise applying the alternating current at a sufficient magnitude so as to induce a force on the first conductor that will produce a detectable measurement signal in the presence of just the earth's magnetic field. Relying on just the earth's magnetic field a current in the order of a few amps may be sufficient to generate a detectable signal, for instance an alternating current of 3 amps or greater has been shown to provide a detectable signal on the optical fibre and in some well adjusted embodiments current of 1 amp or greater may be sufficient. When using the earth's magnetic field the optical fibre and coupled first conductor may be arranged in a desired alignment to the prevailing magnetic field direction for at least parts of the deployment of the optical fibre and first conductor.

It will be appreciated that any other source of magnetic fields that is already present in the environment will also contribute to the ambient magnetic field. For instance the presence of any permanent magnetic material in the environment will also impact on the ambient magnetic field. The ambient magnetic field may therefore be greater at some parts of the environment than others due to the presence of such material in the environment. Likewise, if the environment near the fibre optic cable includes power cables or other significant conductors carrying current, such other conductors in the environment may generate a magnetic field when operational.

In addition the magnetic field generated by the alternating current flowing in the first conductor may, in some instances, induce secondary magnetic fields in materials that can be, at least partially, magnetised and the presence of such secondary magnetic fields may also influence the magnetic field acting on the first conductor in use.

In some applications, as will be described later, the method may comprise analysing the measurement signals to detect any variation which may be due to locally varying magnetic field strength. Such a method may be employed as part of a magnetic field detection method for instance as part of a method of detecting ferromagnetic material and/or objects.

In some embodiments the method may involve specifically arranging at least a second element that, in use, generates a magnetic field in the vicinity of the first element. In other words rather than rely (solely) on the ambient magnetic field, for example the earth's magnetic field, the method may utilise at least one element that has been arranged to apply a magnetic field to the conductor in use. The presence of the second element results in a magnetic field acting on the first conductor that is greater than would have been the case in the absence of the second element, i.e. the ambient field due to the environment. Increasing the overall magnetic field strength in the vicinity of the first conductor may increase the expected measurement signal for a given alternating current magnitude. Thus increasing the magnetic field strength can increase the likely detected signal (e.g. improve the signal to noise ratio of the measurement signal) and/or reduce the current requirements. Additionally using a second element to generate a magnetic field can allow the orientation and/or strength of the magnetic field to the first conductor to be known/controlled. If the orientation and strength of the magnetic field is known the force induced on the first conductor for a given current may also be known, thus allowing the application of one or more known force(s). As will be described later this can allow for calibration of the fibre optic sensor.

The second element may be deployed so that the optical fibre and first conductor (which are coupled together) may move relative to the second element and the freedom of movement depends on the environment. Thus the second element may be deployed as a separate item in the environment to the first conductor/optical fibre.

For example the optical fibre will typically be part of a fibre optic cable, i.e. a structure including one or more optical fibres with an outer jacket. In some embodiments the second element may be arranged externally to the fibre optic cable structure, which may comprise the optical fibre alone or both the optical fibre and the first conductor. The second element could be deployed alongside the cable structure so that in use the force induced on the first conductor causes the cable structure to try to move in the environment.

In some embodiments however the second element may form part of the fibre optic cable structure, with the structure being arranged to allow at least some motion of the first conductor (and hence the optical fibre) relative to the second element. Including the second element in the cable structure will allow for ease of deployment as only a single cable needs to be deployed in the environment. Further including the second element in the same cable structure as the first conductor may avoid any significant variations in positioning of the first conductor within the magnetic field generated by the second element. The force induced by the magnetic field of the second element on the first conductor will lead to a varying strain on the first conductor, and optical fibre, which may still depend on the environment. For instance the optical fibre may be deployed within a deformable material within the cable structure so that the coupling of the environment to the cable structure influences the amount of deformation of the deformable material.

The second element may comprise a permanent magnetic material, i.e. a material that creates its own persistent magnetic field. Thus there may be one or more permanent magnets deployed along the length of the optical fibre.

In some embodiments at least some permanent magnets may be coupled to the optical fibre, e.g. via springs or other similar elastic attachment that allows at least some movement between the magnet and the optical fibre. The presence of the permanent magnets increases the magnetic field strength in the vicinity of the magnet which leads to a greater measurement signal at said locations. Attaching the magnets to the optical fibre (typically the fibre optic cable), may ease in deployment and ensure correct default positioning of the permanent magnet relative to the first conductor. As mentioned the attachment, e.g. spring, will allow relative motion of the fibre optic and the magnet. Using a spring, for example, could increase sensitivity to specific frequencies at the locations of the permanent magnets. The resonant frequency may also change with change in surroundings.

In some embodiments the second element may comprise a second conductor through which a current flows in use. Thus the method may comprise applying a current to a second conductor in the vicinity of the first conductor. The second conductor may be arranged to run along the length of at least part of the optical fibre which is coupled to the first conductor. In some embodiments the second conductor may be arranged to have substantially the same geometry as the first conductor, for example the first and second conductors may be substantially parallel or deployed in the same meandering path or coiled arrangement. In other embodiments however the second conductor may be arranged to run along at least some of the same path of the first conductor but may have a different geometry to the first conductor, for instance the first conductor may run in a path that follows the path of the optical fibre whereas the second conductor may be arranged in a coiled or helical arrangement.

In use a direct current may be applied to the second conductor to provide a relatively constant magnetic field.

In some embodiments the method may comprise varying the magnitude of the direct current applied to the second conductor. The magnitude of the direct current may be changed, for instance progressively increased by ramping the current or incrementing step wise changes. The direct current supplied may for instance be varied to determine the lowest current required that produces an acceptable measurement signal. Alternatively scanning the direct current level required for a certain measurement signal may form part of the determination of environmental characteristic.

Where the first and second elements are both conductors an alternating current may alternatively be applied to the second conductor with a direct current applied to the first conductor. Applying the alternating current to the second conductor will, in effect, create a varying magnetic field which thus induces a varying force on the first conductor (and hence optical fibre) through which a direct current is flowing. The varying current may therefore be applied to the second element whilst the current of the first conductor is kept constant.

Applying a direct current to the first conductor and varying the current to the second conductor may ensure that any effects from the earth's magnetic field may be isolated from the measurement signal (which results from the varying stimulus induced on the optical fibre). The direct current flowing in the first conductor will result in a force being induced on the first conductor (and hence on the optical fibre) due to the presence of the earth's magnetic field. However with a direct current applied to the first conductor the force induced by the earth's magnetic field (which can be considered substantially constant) will be a substantially constant force. Thus the contribution of the earth's magnetic field, if detectable, will appear as a DC offset in the detected measurement signal. The variation in force on the first conductor will thus principally arise from the varying magnetic field generated by the second conductor. In some embodiments isolating the (potentially unknown) effects of the earth's magnetic field from the measurement signal may improve signal to noise ratio and thus in some embodiments it may be preferred to apply a direct current to the first conductor.

In other embodiments however the currents through both the first and second conductors may be varied. For instance both currents could be alternating currents with a predetermined phase difference to induce a desired varying force and/or alternating currents with different frequencies could be applied to the two conductors to generate a varying force that exhibits beats.

It should be noted that a direct current could be applied to the first conductor coupled to the optical fibre to detect the presence of any varying magnetic fields in the environment. For instance for detection and/or monitoring of AC power cables a direct current could be applied to the first conductor. If a varying magnetic field is present, such as generated by an AC power cable, there will be a varying force induced on the first conductor and hence the optical fibre leading to a detectable measurement signal.

The first conductor may comprise an elongate conductor, such as a conductive wire, which runs along the length of at least part of the optical fibre although other forms of conductor may be used. In some embodiments the first conductor may have an arcuate cross-section and may be arranged to at least partly surround the optical fibre. The first conductor could be formed with the optical fibre in a cable structure. Some fibre optic cable structures are known which comprise a metallic sleeve surrounding an optical fibre core, with the metallic sleeve being provided as a protective jacket for the optical fibre. Such a cable could be arranged with the metallic sleeve used to carry the alternating electric current.

There may be a single first conductor which runs along the path of, and is coupled to, the optical fibre.

The first conductor may comprise an elongate section coupled to the optical fibre of greater than 100 m in length or greater than 500 m in length or greater than 1 km in length. Preferably the first conductor may run for at least the length of the section of fibre which is deployed for sensing—which may be several kilometers in length. Applying the alternating current to the first conductor thus induces a stimulus on the whole length of fibre in the area of interest. The measurement signals from a plurality of sensing portions of fibre can therefore be produced and analysed to determine information about the local environmental characteristics for each sensing portion. The method thus provides a distributed fibre optic sensor of environmental characteristics.

However in some embodiments the first element may comprise a plurality of first conductors, each coupled to the optical fibre at different locations along its length and each being arranged to receive an electric current in use. The different first conductors may each be connected to individual current driving circuits so that a current can be applied to each conductor individually and/or at least some of the conductors may be connected in series, for instance by suitable connecting wires or the like which are not coupled to optical fibre. In this way multiple different sections of the optical fibre can be coupled to elements to which a force may be induced.

In some embodiments the first conductor may comprise a magnetostrictive material, for instance nickel or steel. Magnetostrictive materials are materials whose dimensions may vary in the presence of a magnetic field. In use the current applied to the first conductor will generate a magnetic field which will induce magnetostriction in the magnetostrictive material. As the current varies the magnetostriction will also vary with the result that a varying force is applied to the first conductor in accordance with the varying current which can lead to a detectable measurement signal. A similar effect could be achieved by ensuring the first conductor is coupled to a suitable magnetostrictive material.

In another embodiment the first element may comprise at least one magnetic element responsive to an applied magnetic field and the method comprises applying the varying current so as to vary the magnetic field acting on the first element. The magnetic element responsive to an applied magnetic field is an element that experiences a force in the presence of a magnetic field. The magnetic element may comprise a permanent magnetic material, i.e. a material that creates its own persistent magnetic field, and/or may comprise a material that exhibits paramagnetism and/or a material that exhibits diamagnetism. The at least magnetic element could be included within a fibre optic cable structure with the optical fibre or coupled to the optical fibre.

In this embodiment the method may comprise applying an alternating current to a second element to generate a varying magnetic field. The second element may comprise a conductor deployed in the vicinity of the magnetic element and optical fibre. For example the second element may comprise an elongate conductor running along at least part of the length of the optical fibre.

As described above embodiments of the present invention may therefore involve applying a varying current to a conductor, which may be either the first element itself and/or a conductor arranged so as to apply a variable magnetic field to the first element. In any of these embodiments one or more conductors may run along a significant length of the optical fibre.

To allow a current to flow both ends of such a conductor must be connected into a suitable circuit. In some embodiments one end of the conductor may be connected to a local potential, for instance a local ground or reference potential at the end of the conductor. Thus the varying current, such as an alternating current, may be applied by generating an appropriately varying driving voltage at the other end. This may be useful where the conductor runs alongside the optical fibre for a significant length. One end of the conductor (the proximal end) may be readily located near the end of the optical fibre which is connected to the interrogator. Thus applying a driving voltage may be relatively easy to achieve. However the other end of the conductor may be located a significant distance away and in many fibre optic sensing systems the distal end of the fibre is not required to be connected to anything. The distal end of the conductor may therefore be connected to a local reference potential at that location.

In some embodiments however a conductor, for instance a conductor forming the first element, may be connected to, or form part of, a conductor that doubles back to the proximal end of the fibre so that both ends of the circuit are available at the proximal end of the fibre.

In such an arrangement care must be taken with the arrangement of the various current paths.

For example consider a first conductor coupled to the optical fibre. In use the first conductor may form part of a first current path from suitable driving circuitry to the end of the optical fibre. There may also be a second current path from the end of the optical fibre back to the driving circuitry. It will be appreciated that, as the first current path and second current path from part of an overall current path and run in generally opposite directions, the current flowing in the first current path at any time will flow in generally the opposite direction to the current in the second current path and will be of substantially similar magnitude. Thus any force induced on the first current path in the presence of an external magnetic field will be substantially opposite to that induced in the second current path.

The second current path should therefore be substantially mechanically uncoupled from the first current path. In other words the first conductor of the first current path should be free to move in the environment relative to the second current path. It will be understood that the first current path and second current path will be connected at some point or via some intermediate current path and thus there will be some degree of coupling between the conductors forming the current paths at this point, but away from such transition zone the current paths are substantially uncoupled as described.

In some embodiments the second current path may be arranged sufficiently far away from the first current path so as to not substantially interfere with the force induced on the first current path (i.e. the first conductor) in use. It will be appreciated that in use a current will flow in the second current path whenever a current also flows in the first current path. The current flowing in the second current path will generate a magnetic field. The second current path may therefore be sufficiently removed from the first current path so that, at the first current path, any contribution to the magnetic field from the second current path is lower than the contribution from other sources—such as the ambient magnetic field and/or any second element specifically deployed to produce a magnetic field on the first conductor as described above.

Thus, for example, in the embodiment where the method relies on the earth's magnetic field inducing a force on the first conductor in use, the second current path should be located far enough away from the first conductor so that any contribution from the second current path (at the first conductor) is lower than that of the earth's magnetic field. For example, in a wire carrying 3 A current, the magnetic field strength is approximately equivalent to that of the earth at a distance of about 7.5 mm. Therefore the second current path may be arranged to be much further away than this distance from the first current path, for instance at least a few centimeters.

In another embodiment however the second current path may be arranged so that the magnetic field generated by the second current path is deliberately used to at least aid in generating the variable force on the first conductor. In other words, considering the embodiments described above with both first and second conductors, the first and second conductors could be electrically connected to form part of the same circuit. In other words the first conductor may form at least part of the first current path and the second conductor may form at least part of the second current path.

In this embodiment the current flowing in the first conductor will thus generally be in the opposite direction to the current flowing in the first conductor (depending on the exact deployment of the two current paths). As an example the first and second conductors may be substantially parallel to one another. As the current in both conductors vary the force induced on the first conductor will also vary. In this arrangement the force between the first and second conductors may always be repulsive and where an alternating current with a defined frequency is applied the measurement signal will correspond to double the applied frequency.

Whatever the spatial arrangement of the second current path in respect to the first current path the two current paths may comprise different sections of a single elongate conductor such as a wire. For instance part of the conductive wire could be attached to or deployed inside the fibre optic cable structure to provide the first current path. The conductive wire may emerge from the fibre optic cable at some point and double back to the start of the fibre to provide the second current path. Alternatively the second current path may be provided by one or more conductors which are electrically connected to the first conductor.

The embodiments described above thus induce a varying force on a first element which is coupled to the optical fibre. This will result in at least some force being imparted to the optical fibre in a manner that can be readily detected to provide a measurement signal. Preferably the method comprises generating a measurement signal from a plurality of sensing portions of said fibre. As described above the first element may be elongate and extend for a considerable length of the fibre—thus in use a force may be induced over a considerable length of fibre which can be interrogated to provide a plurality of sensing portions. Each sensing portion will thus generate a measurement signal indicative of the variation in the backscattered radiation corresponding with said electric current applied for that sensing portion. Thus the method provides a distributed environmental fibre optic sensor.

The measurement signals may be generated by using distributed acoustic sensing techniques and thus the method may comprise interrogating the fibre and analysing the detected back-scatter to provide distributed acoustic sensing when said alternating current is applied.

As mentioned previously the measurement signal(s) can be used to provide information about the environment in which the optical fibre is located. The method therefore comprises analysing at least one measurement signal to determine a characteristic of the environment in which the corresponding section of optical fibre is deployed.

In one embodiment the characteristic may be mechanical (or acoustic) impedance of the environment, i.e. the resistance of the environment to movement.

For instance if the optical fibre is relatively unconstrained by the environment the force induced on the first element and hence the optical fibre may lead to a first measurement signal. However if the optical fibre is tightly buried or otherwise constrained by the environment the freedom of movement of the optical fibre may also be constrained and thus the detected response to the varying force may have a different characteristic, such as a reduced measurement signal level. Thus a part of a fibre which is deployed on the ground but relatively unconstrained may generate a different measurement signal to a part of a fibre which is immersed in water or buried. Further a part of a fibre which is loosely buried, for instance in sand, may generate a different signal to a fibre which is tightly buried, for instance in heavy clay like ground.

Thus by looking at the measurement signal indicating the detected variation in backscattered radiation it may possible to determine an indication of the impedance of the environment in which the fibre is deployed. For example sections of the fibre which exhibit a first measurement signal level in response to the applied varying electric current may correspond to areas of relatively low impedance and sections of the fibre which exhibit a second, different, measurement signal level may correspond to areas of relatively high impedance.

A measure of impedance may be useful in a number of different applications. For instance an optical fibre may be embedded within a structure to provide structural monitoring. Detecting a significant change in impedance over time could indicate that the condition of the structure is changing. A fibre deployed along the ground, for instance along the route of a transport link such a road or railway line could be monitored to detect any significant change in impedance which could indicate that the fibre has become covered, for instance as a result of significant snow fall, land slip or sand cover depending on the general location. Detection of covering of the optical fibre may indicate a potential obstruction of the transport link. An optical fibre which is deployed on the ground or which is buried loosely in the ground, or deployed in a cavity which is open to the environment, may be monitored to detect a change of impedance due to being submerged in water thus serving a detector for water-logging or flooding.

Additionally or alternatively the method may be used to determine the magnetic properties of the environment, i.e. the characteristic of the environment is the local magnetic properties. As described above in embodiments which rely predominantly on a local magnetic field acting on the first element any variation in local magnetic field strength may lead to different measurement signals. These variations may be due to the presence or permanent magnetic materials or power cables or the like or the presence of objects in which a secondary magnetic field is induced. A sensor according to this aspect of the invention may therefore be employed for detection, for instance detecting the presence of metallic and/or ferromagnetic objects and/or power cables or other conductors. Additionally or alternatively the method may comprise monitoring for any variation in the local magnetic characteristics. Monitoring for any changes in magnetic properties may be useful in monitoring of structures comprising metallic items, such as structural beams or railway tracks for example. The contribution to the ambient field from the metallic item, e.g. beam or track, may change if, for instance, the item cracks. This may result in change in the local field properties which can be detected. Likewise the magnetic contributions from power cables could be monitored for any disturbance indicative of a potential problem.

The method may comprise comparing different measurement signals from different parts of the optical fibre, and/or measurement signals from a given section of the optical fibre acquired at different times, to give a relative measure of the characteristic of the environment. For example the measurement signals could be compared to determine if one part of the fibre is within an environment of relatively higher impedance than another area and/or whether the relative impedance of a given section of fibre has changed over time. This could for instance be useful for detecting whether the environmental conditions have changed.

The method may additionally or alternatively comprise analysing the measurement signal from a given section of fibre to estimate the present environmental characteristic. For instance in some embodiments the detected measurement signals when the alternating current is applied may be compared with a known or expected signal characteristic. As described above, in some embodiments, the step of applying the alternating electric current may result in a relatively well known force being induced on the first element and the optical fibre. If the degree of force applied is known, at least to a certain accuracy, the expected variation in the response of the optical fibre in certain environmental conditions may also be known, e.g. the expected variation if the optical fibre is laid on flat ground and unconstrained. Comparing the actual response, i.e. the detected measurement signal, with the expected response may provide an indication of the absolute characteristics of the environment.

The optical fibre with the first element may be principally deployed as an environmental sensor, i.e. the sensor is principally interrogated with the varying current applied (to determine characteristic of the environment) and is not typically interrogated without the varying current applied. The varying, e.g. alternating current may be applied continually or periodically (as required) to acquire measurement signals.

In some embodiments however the optical fibre may be used for at least one additional sensing function. For example the optical fibre could be interrogated without the varying current being applied to provide at least a first sensing function and could separately be interrogated with the varying current applied to determine the characteristic of the environment. The first sensing function may conveniently comprise distributed acoustic sensing. In this embodiment the steps of interrogating the fibre may be substantially the same both with and without the varying current applied. Thus the optical fibre may be interrogated without the varying current applied to measure acoustic signals incident on the optical fibre. Periodically however the varying current, e.g. an alternating current, could be applied to allow for determination of the characteristics of the environment. In some applications however the first sensing function may comprise some other sensing function such as a distributed temperature sensing (DTS) for example. The method may therefore comprise interrogating the optical fibre to provide DTS without the varying current applied and periodically applying the varying current and interrogating the optical fibre to provide a measurement signal using DAS type techniques. This may involve varying the form of the interrogating radiation and/or processing between implementing the first sensing function and detecting the environmental characteristics.

Where the optical fibre is used for a first sensing function in addition to the sensing of the environmental characteristic the determination of the environmental characteristic may be used to calibrate the measurements of the first sensing function for variation in environmental properties. For example for a DAS sensor the mechanical impedance of the environment may be related to the response of the sensor to a given acoustic stimulus. Thus if the sensing optical fibre is deployed such that the properties of the local environment vary along the length of the fibre then the DAS signals detected from a given stimulus may also vary along the fibre. Performing the method of the present invention to determine variations in local environmental properties may allow a relative calibration between various sections of the fibre. Periodically sensing the environmental characteristics may also allow for variations in the environment over time to be calibrated for. For instance a fibre deployed on the ground or buried in the ground may exhibit a different response depending on how dry or wet the ground is, whether the ground is frozen and/or whether there is snow on the ground. All of these conditions may be determined by performing environmental sensing according to methods described previously.

The calibration may be a relative calibration, for instance by determining any relative changes in the environmental characteristic over time at a given location and/or any variation between sensing portions of the fibre with the varying current applied. As mentioned previously however in some embodiments, where the magnetic field applied to the first element and hence the force induced is known, the calibration could be an absolute calibration.

This means that a fibre deployed in an environment of interest can be readily calibrated. By using the methods of the present invention a known stimulus can be applied to at least one section of the optical fibre, which may comprise substantially the whole of the sensing fibre. The stimulus is applied by inducing the force on the first element and thus can be applied to the whole fibre simultaneously by applying the varying current. This may require access to one end of the optical fibre only.

The method may therefore comprise determining measurement signals as described above and analysing the measurement signals to determine a calibration factor to be applied to one or more sensing of portion of the optical fibre when used for an additional sensing function.

In some embodiments, where the varying current is an alternating current, the method may comprise varying at least one of the frequency and/or magnitude of the alternating current applied. Varying the frequency and/or magnitude of the alternating current may help in identifying the measurement signal due to the force induced on the first element and hence the optical fibre. For instance the backscatter radiation signals could be correlated with a frequency sweep used. Additionally or alternatively however varying the frequency of the alternating current may provide additional information about the environmental properties. For instance harmonics may be present in the measurement signals at certain frequencies which may be related to properties of the environment. Analysing at least one measurement signal may therefore comprise applying frequency analysis to the measurement signal.

The frequency of the alternating current, whether or not varied in use, may be chosen to provide detectable measurement signals with a good signal to noise ratio. The amplitude of the measurement signal may decrease with increasing frequency, for example due to the inertia of the fibre optic cable. The alternating current frequency may therefore be at or below 300 Hz, say at or below 100 Hz. However low frequencies may be more noisy. Thus the alternating current frequency may be at or above 1 Hz, or for example at or above 10 Hz.

The foregoing has been described in terms of determining the inherent properties of the environment, such as mechanical impedance for example. In some embodiments however the method may be used to provide additional sensing capability by using a material whose properties vary in accordance with a desired parameter to be sensed to modify the environmental characteristics of the optical fibre. Thus for instance the optical material and first material may be deployed within or coupled to a material whose impedance varies in accordance with a first parameter it is desired to monitor. The first parameter could be, for example, temperature, humidity, UV radiation or pressure. For example the material could comprise a gel whose viscosity varies with temperature or a polymer material whose pliability varies with UV exposure. The material may be chemically sensitive materials which react to particular chemicals, for instance to detect chemical leaks. The material could be sensitive to ionising radiation to act as a radiation detector. In some embodiments the change in impedance could be well defined with respect to the first parameter, for example a change in viscosity could occur at a well-defined temperature (like melting wax for example), which would allow use as a calibration point.

The optical fibre is thus deployed, in least in one location, coupled to or within a material whose impedance properties, i.e. stiffness, viscosity, pliability etc. vary in accordance with the desired parameter. In use the optical fibre is interrogated as described above to determine the impedance of the environment—which is determined by the properties of the first material, which in turn depends on the sensed parameter. Thus in some embodiments the optical fibre and first element may be coupled to a material whose properties vary in accordance with a first parameter to modify the environmental characteristics of the optical fibre. The method may comprise determining the impedance of the environment and hence provide an indication of the first parameter.

In general therefore the method involves coupling an optical fibre to a first element which is responsive, in use, to an applied electromagnetic field and supplying an alternating current to a conductor, which may or may not form part of the first element, so as to induce a force on the first element and thus the fibre. By generating a force on the fibre in situ various information about the environment can be determined.

Providing an impedance sensor is one particularly useful aspect of the present invention and thus one aspect of the invention relates to a method of impedance sensing comprising interrogating an optical fibre with radiation to provide distributed acoustic sensing, whilst applying alternating varying current so as to induce a force on a first element coupled to optical fibre. The first element may comprise a conductor and the method may comprise applying the varying current, e.g. an alternating current, to the first element conductor in the presence of a magnetic field.

Providing a magnetic sensor is another particularly useful aspect of the present invention and thus one aspect of the invention relates to a method of magnetic sensing comprising interrogating an optical fibre with radiation to provide distributed acoustic sensing, whilst applying a current to a conductor coupled to the optical fibre. In the presence of any magnetic fields a force will be induced on the conductor and hence the optical fibre. The applied current may be a varying current as described previous which allows for detection/monitoring of magnetic fields, including static or substantially constant magnetic fields. However if an application only required detection of varying or dynamic magnetic fields a direct current could be applied to the conductor.

In particular the method of magnetic sensing may be used for object detection. The magnetic sensing method may also be used for structural monitoring of metallic structures.

Calibrating a distributed fibre optic sensor represents another particularly useful aspect of the present invention and thus one aspect of the invention relates to a method of calibrating a distributed fibre optic sensor having a sensing optical fibre deployed in an area of interest, the method comprising interrogating said optical fibre with radiation to provide distributed acoustic sensing, whilst applying a varying current so as to induce a force on a first element coupled to optical fibre. The first element may comprise a conductor and the method may comprise applying the varying current, e.g. an alternating current, to the first element conductor in the presence of a magnetic field. The calibration method may further comprise analysing the detected acoustic signals to determine at least one calibration factor.

Another aspect of the invention relates to a method of sensing a first parameter in a location of interest comprising deploying an optical fibre in the area of interest, wherein the optical fibre to coupled to a first element responsive to electromagnetic field and also coupled to, or deployed within, a first material that has at least one impedance property that varies in accordance with said first parameter, and interrogating said optical fibre with radiation to provide distributed acoustic sensing, whilst applying a varying current so as to induce a force on the first element.

The invention also relates to a sensor apparatus. Thus in another aspect of the invention there is provide a sensor apparatus comprising: an optical fibre, at least part of which is mechanically coupled to at least a first element responsive, in use, to electromagnetic fields; an interrogator unit for interrogating said optical fibre with optical radiation and an electrical circuit for generating a varying electric current so as to induce a varying force on said first element. The apparatus may further comprise a processor configured to analyse optical radiation backscattered from within said optical fibre to determine a measurement signal indicative of a variation in the backscattered radiation corresponding with said electric current applied.

The apparatus according to this aspect of the invention offers all of the same advantages and can be used in all of the same ways as described above.

In particular the first element may comprise a first conductor. The apparatus may be arranged so that a current flows in the first conductor in use.

The electrical circuit may be configured to generate the varying current, e.g. an alternating electric, current in the first conductor. As described above the sensor apparatus may rely on an ambient magnetic field to generate a force on the first conductor when the alternating current flows. In some embodiments however the sensor apparatus may comprise at least a second element that, in use, generates a magnetic field in the vicinity of the first element. The second element may forms part of a fibre optic cable structure with the optical fibre and first conductor, the structure being configured to allow at least some motion of the first conductor relative to the second element. The second element may comprise a permanent magnetic material, for instance one or more permanent magnets deployed along the length of the optical fibre and first conductor. In some embodiments the second element comprises a second conductor. The sensor apparatus may comprise an electric circuit for generating a current in the second conductor so as to generate a magnetic field. The sensor apparatus may be configured to generate a direct current to in the second conductor and an alternating current to the first conductor. Alternatively a direct current may be generated in the first conductor and an alternating current is generated in the second conductor.

The first conductor may be an elongate conductor, such as a conductive wire, which runs along the length of at least part of the optical fibre. The first conductor may alternative have an arcuate cross-section and may, for instance at least partly surround the optical fibre.

The first conductor may be formed with the optical fibre in a cable structure.

The first conductor may comprise an elongate section coupled to the optical fibre of greater than 1 km in length.

In some embodiments the first element may comprise a plurality of first conductors, each coupled to the optical fibre at different locations along its length and each being arranged to receive an electric current in use.

In one embodiment the first element comprises at least one magnetic element responsive to an applied magnetic field. The electrical circuit may be arranged to generate the varying current, e.g. an alternating current, so as to vary the magnetic field acting on the first element. The magnetic element may comprise at least one of: permanent magnetic material; a material that exhibits paramagnetism or a material that exhibits diamagnetism. Said at least one magnetic element may be incorporated in a fibre optic cable structure with the optical fibre. The alternating current may be applied to a second element to generate a varying magnetic field. The second element may comprise a conductor deployed in the vicinity of the magnetic element and optical fibre.

The interrogator unit and processor may be configured to generate a measurement signal from a plurality of sensing portions of said fibre. The interrogator unit may be a distributed acoustic sensing interrogator unit.

The processor may be arranged to analyse the measurement signals according to any of the methods described above.

The processor may be configured to determine the mechanical impedance of the environment. The processor may be configured to determine the local magnetic properties of the environment, for instance to detect objects such as: metallic objects, ferromagnetic objects or conductors.

The processor may be arranged to perform structural monitoring and the optical fibre may be embedded within or adjacent a structure to provide structural monitoring.

The interrogator unit and processor may be configured to interrogate the optical fibre without the alternating current applied to perform a first sensing function. The processor may be configured to calibrate the result of the first sensing function based on the measurement signal acquired when the varying current is applied. The processor may be configured to analyse the measurement signals to determine a calibration factor to be applied to one or more sensing of portions of the optical fibre when used for the first sensing function.

The electrical circuit may be configured to apply alternating current as the varying current. The electrical circuit may be configured to vary at least one of the frequency and/or magnitude of the alternating current applied. The processor may be configured to correlate the measurement signals with a frequency modulation of the alternating current.

The optical fibre and first element may also be coupled to a material whose properties vary in accordance with a first parameter to modify the environmental characteristics of the optical fibre. The first parameter may be one of, for example, temperature, humidity, UV radiation or pressure. The processor may be configured to determine the impedance of the environment and using the impedance as an indication of the first parameter.

The invention also relates to a computer program, which may be stored on a non-transitory computer readable storage medium, which when run on a suitable computer, for instance a controller of a fibre optic sensing apparatus, performs any of the methods as described above.

The invention also relates to the form of fibre optic cable suitable for determining the properties of the environment in which the optical fibre is deployed. In a further aspect of the present invention therefore there is provided a fibre optic cable for sensing the environmental characteristics of the environment in which is deployed comprising an optical fibre coupled to a first element responsive, in use, to electromagnetic fields.

The fibre optic cable may be implemented in any of the ways as described previously. In particular the first element may comprise a first conductor. The first conductor may be an elongate conductor, such as a conductive wire, which runs along the length of at least part of the optical fibre. The first conductor may alternative have an arcuate cross-section and may, for instance at least partly surround the optical fibre. The first conductor may comprise an elongate section coupled to the optical fibre of greater than 1 km in length.

In some embodiments the first element may comprise a plurality of first conductors, each coupled to the optical fibre at different locations along its length.

The cable may additionally comprise a second element that, in use, generates a magnetic field in the vicinity of the first element, the structure being configured to allow at least some motion of the first conductor relative to the second element. The second element may comprise a permanent magnetic material, for instance one or more permanent magnets deployed along the length of the optical fibre and first conductor. In some embodiments the second element comprises a second conductor.

In one embodiment the first element comprises at least one magnetic element responsive to an applied magnetic field. The magnetic element may comprise at least one of: permanent magnetic material; a material that exhibits paramagnetism or a material that exhibits diamagnetism. The cable may further comprise a second element that, in use, generates a varying magnetic field. The second element may comprise a conductor.

The optical fibre and first element may also be coupled to a material whose properties vary in accordance with a first parameter to modify the environmental characteristics of the optical fibre. The first parameter may be one of, temperature, humidity, UV radiation or pressure. The processor may be configured to determine the impedance of the environment and using the impedance as an indication of the first parameter.

In general the invention relates to the use of a varying current to generate a varying force on an optical fibre of a fibre optic sensor by inducing a varying force on a first element response to electromagnetic fields which is coupled to said optical fibre.

DESCRIPTION OF THE DRAWINGS

The invention will now be described by way of example only, with reference to the accompanying drawings, for which.

DESCRIPTION OF THE INVENTION

Embodiments of the present invention use the techniques of fibre optic distributed acoustic sensing to provide detection and/or monitoring of the characteristics of the environment within which a sensing fibre is deployed.

Figure 1:
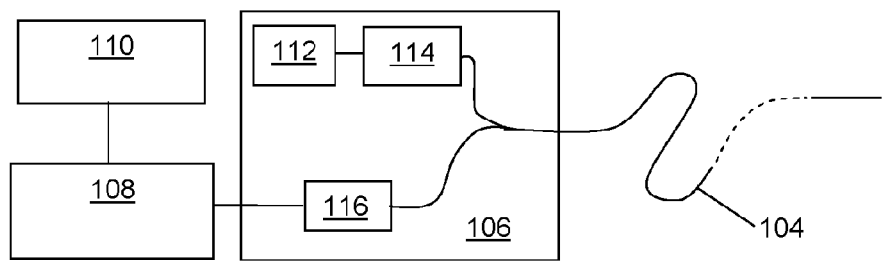
FIG. 1 illustrates a conventional DAS sensor apparatus.

FIG. 1 shows a schematic of a conventional distributed fibre optic sensing arrangement. A length of sensing fibre 104 is removably connected at one end to an interrogator 106. The output from interrogator 106 is passed to a signal processor 108, which may be co-located with the interrogator or may be remote therefrom, and optionally a user interface/graphical display 110, which in practice may be realised by an appropriately specified PC. The user interface may be co-located with the signal processor or may be remote therefrom.

The sensing fibre 104 can be many kilometers in length and can be, for instance 40 km or more in length. The sensing fibre may be a standard, unmodified single mode optic fibre such as is routinely used in telecommunications applications without the need for deliberately introduced reflection sites such a fibre Bragg grating or the like. The ability to use an unmodified length of standard optical fibre to provide sensing means that low cost readily available fibre may be used. However in some embodiments the fibre may comprise a fibre which has been fabricated to be especially sensitive to incident vibrations. In use the fibre 104 is deployed in an area of interest to be monitored.

In operation the interrogator 106 launches interrogating electromagnetic radiation, which may for example comprise a series of optical pulses having a selected frequency pattern, into the sensing fibre. The optical pulses may have a frequency pattern as described in GB patent publication GB2,442,745 the contents of which are hereby incorporated by reference thereto, although DAS sensors relying on a single interrogating pulse are also known and may be used. Note that as used herein the term "optical" is not restricted to the visible spectrum and optical radiation includes infrared radiation and ultraviolet radiation. As described in GB2,442,745 the phenomenon of Rayleigh backscattering results in some fraction of the light input into the fibre being reflected back to the interrogator, where it is detected to provide an output signal which is representative of acoustic disturbances in the vicinity of the fibre. The interrogator therefore conveniently comprises at least one laser 112 and at least one optical modulator 114 for producing a plurality of optical pulses separated by a known optical frequency difference. The interrogator also comprises at least one photodetector 116 arranged to detect radiation which is Rayleigh backscattered from the intrinsic scattering sites within the fibre 104. A Rayleigh backscatter DAS sensor is very useful in embodiments of the present invention but systems based on Brillouin or Raman scattering are also known and could be used in embodiments of the invention.

The signal from the photodetector is processed by signal processor 108. The signal processor conveniently demodulates the returned signal based on the frequency difference between the optical pulses, for example as described in GB2,442,745. The signal processor may also apply a phase unwrap algorithm as described in GB2,442,745. The phase of the backscattered light from various sections of the optical fibre can therefore be monitored. Any changes in the effective optical path length within a given section of fibre, such as would be due to incident pressure waves causing strain on the fibre, can therefore be detected.

The form of the optical input and the method of detection allow a single continuous fibre to be spatially resolved into discrete longitudinal sensing portions. That is, the acoustic signal sensed at one sensing portion can be provided substantially independently of the sensed signal at an adjacent portion. Such a sensor may be seen as a fully distributed or intrinsic sensor, as it uses the intrinsic scattering processed inherent in an optical fibre and thus distributes the sensing function throughout the whole of the optical fibre. The spatial resolution of the sensing portions of optical fibre may, for example, be approximately 10 m, which for a continuous length of fibre of the order of 40 km say provides 4000 independent acoustic channels or so deployed along the 40 km of fibre.

Embodiments of the present invention use the principle of DAS to detect a measurement signal from sensing portions of the optical fibre in response to a stimulus. However in the embodiments of the present invention the stimulus is not transmitted acoustically to the optical fibre via the environment but instead is generated by using the interaction of electromagnetic fields to induce a force on a first element which is mechanically coupled to the optical fibre. The response of the optical fibre to such a stimulus and/or the strength of the stimulus itself, depends on the characteristics of the environment and thus by analysing the measurement signals from the sensing portions of optical fibre as the stimulus is applied information about the environment in which the optical fibre is deployed may be determined.

Figure 2:
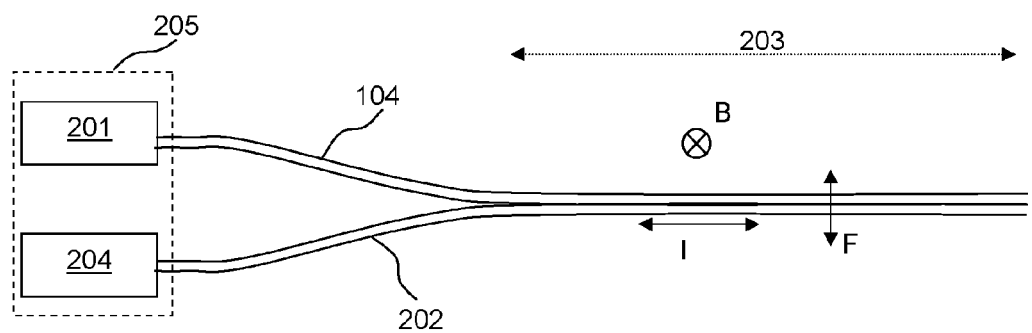
FIG. 2 illustrates an embodiment of the present invention.

FIG. 2 illustrates a first embodiment of the present invention. FIG. 2 illustrates an optical fibre 104 connected to an interrogator 201, which may comprise as DAS interrogator as described above. The optical fibre 104 may be several kilometers in length.

Mechanically coupled to the optical fibre is a first element which is responsive, in use, to electromagnetic fields. In the embodiment shown in FIG. 2 the first element is an elongate conductor 202 which is coupled to at least part of the optical fibre 104. Section 203 indicates the section where the optical fibre 104 and conductor 202 are mechanically coupled to one another. Section 203 may be several kilometers in length and may comprise the entire length of the optical fibre which is used for fibre optical sensing.

The elongate conductor 202 is connected to driving circuitry 204 which is capable of generating a varying current, I, within the elongate conductor. The driving circuitry 204 may be separate to the interrogator 201 but in some embodiments the interrogator 201 and electric circuitry 204 may be implemented in a single control unit 205. To complete the electrical circuit the far end of conductor 204 may be connected to a local reference potential, such a ground, or there may be a return conductor path (not shown) to circuit 204.

When the current, I, which may advantageously be an alternating current, is passed through the conductor 202 in the presence of a magnetic field a force will generated on the conductor as will be understood by one skilled in the art. For the purposes of illustration FIG. 2 shows a plan view of optical fibre 104 and conductor 202 and shows the optical fibre 104 and conductor 202 running in a generally straight line from left to right. For the purposes of illustration a magnetic field B is shown with a field direction into the plane of the page. As an alternating current is applied the current direction will vary, at the AC frequency, from flowing from left-to-right to flowing in the opposite direction. This flow of current in conductor 202 will therefore lead to a force F on the conductor that varies in accordance with the AC current and which, in this illustration, will be in a direction in the plane of paper. The force will vary from being in the top-to-bottom direction to opposite direction.

The effect of the force will therefore be to apply a varying side-to-side strain on the conductor 202, i.e. the conductor 202 will be urged to move in a side to side manner. The conductor 202 is mechanically coupled to the optical fibre 104 in a way such that the force on the conductor also results in a force on the optical fibre. Thus the optical fibre is also induced to move.

Generating the alternating current (i.e. varying current) in the conductor 202 thus results in a vibration/strain stimulus being applied to the conductor and also to the optical fibre 104 which can be detected by the DAS interrogator 106.

The measurement signals detected whilst the current is applied can be used to determine information about the environment in which the optical fibre, and conductor, are deployed.

The measurement signals may be used to determine information about the mechanical impedance of the environment in which the optical fibre is deployed. As the stimulus generated on the optical fibre is not transmitted via the local environment and is instead generated by the interaction of the magnetic field and the applied current the force induced will cause the optical fibre to try move against the surrounding environment. The resistance of the environment to such movement, i.e. the impedance of the environment may thus be determined by looking at the measurement signals detected by the interrogator 106.

Figure 3:
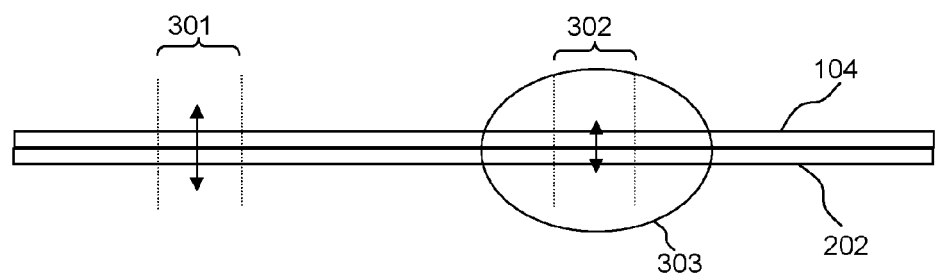
FIG. 3 illustrates impedance sensing according to an embodiment of the invention.

FIG. 3 illustrates this principal. FIG. 3 shows a section of optical fibre 104 which is coupled to conductor 202. FIG. 3 illustrates two separated sensing portions 301 and 302 of optical fibre which may each generate a measurement signal. Sensing portion 301 is in a part of the fibre which is in a first type of environment. For example sensing portion 301 may be located in a section of fibre that is deployed on the ground but is otherwise unconstrained.

Sensing portion 302 is located in a section of fibre deployed in a different type of environment, and in this illustration is deployed within, or under, a medium 303.

To determine the local environmental conditions an AC current is applied to conductor 202 as described previously. For simplicity consider again there is a magnetic field direction into the plane of the paper such that application of the AC current induces a side-to-side motion of the conductor 202 and hence the optical fibre 104.

For sensing portion 301 the optical fibre is relatively unconstrained and thus may be relatively free to move in response to the induced force. Thus the optical fibre at sensing portion 301 may experience a relatively large movement in response to the stimulus induced by the AC current. The movement of the fibre may result in a relatively large path length variation within the fibre and hence a relative large change in the properties of the backscattered radiation from the optical fibre. The DAS interrogator may therefore detect a relatively large amplitude signal at this sensing portion.

However, sensing portion 302 is embedded within or buried under material 303. At this location the movement of the fibre may be impeded by the material 303. As the resulting measurement signal in effect depends on how great a movement is experienced by the optical fibre at this point the resulting measurement signal will therefore be indicative of the mechanical impedance of the material 303. Thus if the material 303 were, say light sand loosely covering the optical fibre 104 then measurement signal from sensing portion 302 may have a first signal level whereas if the material 303 were dense soil tightly packed around the fibre 104, the measurement signal may have a different signal level.

Measuring the impedance of the local environment of the optical fibre may be used for a variety of applications, for instance detecting whether a cable has become buried may be useful for detecting sand coverings on railway lines or snow cover. For a fibre that may be partially submerged a change in impedance could be used to indicate flooding or water-level or simply indicate that an area is water-logged. Impedance sensing may also be used for structural monitoring. The fibre may be embedded within a structure and detection of a change in impedance could be used to detect void formation or the like.

The conductor 202 may be mechanically coupled to the optical fibre in a variety of ways. Any type of mechanical coupling which results in the force on the conductor being transmitted to the optical fibre may be used.

Figure 4:
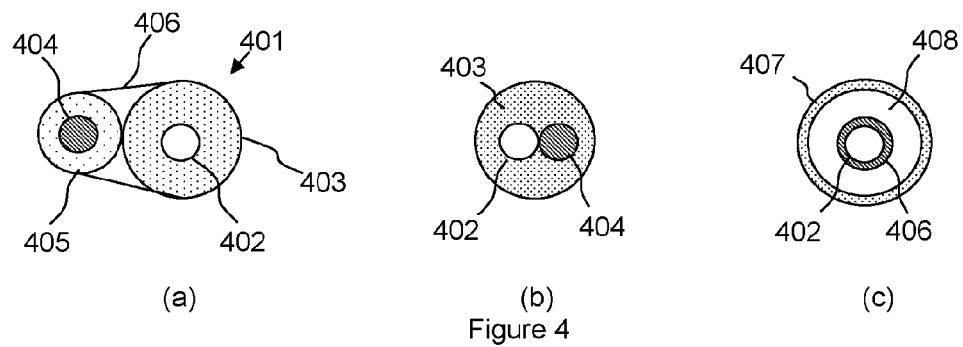
FIG. 4 illustrates various embodiments of an optical fibre coupled to a conductor.

It will be appreciated that an optical fibre is typically deployed in a fibre optic cable structure which may comprise one or more jacket materials to provide protection for the optical fibre. In some cable designs there may be more than one optical fibre. The conductor may therefore be external to and attached to the fibre optic cable, for instance by suitable clamping or bonding. FIG. 4a shows a cross section of a fibre optic cable structure 401 having an optical fibre 402 disposed within at least one jacket layer 403. Attached to the outside of the fibre optic cable 401 is a conductive wire, comprising a conductive core 404 in at least one insulating jacket 405. The conductive wire may be attached to the fibre optic cable by attachment 406 which may be comprise adhesive, ties and/or clamps for example.

FIG. 4b shows a cross section of another embodiment of a cable structure wherein the conductor is arranged within the fibre optical cable structure. The optical fibre 402 may be arranged with a jacket material 403 with a conductive core 404. The jacket material 403, which may comprise one or more layers, may provide protection and may also provide the mechanical coupling of the conductor and optical fibre.

FIG. 4c shows a cross section of a cable according to another embodiment. Here the optical fibre 402 is surrounded by a metal sleeve 406. Such cable structures exist and usually the metal sleeve 406 is provided for protection. However it may also be used as an arcuate conductor which surrounds the optical fibre. The cable may have an outer jacket layer 407 and intermediate material 408 which may be relatively stiff or rigid so that movement of the conductor 406 results in movement of the cable relative to the environment.

Referring back to FIG. 2 the magnetic field B may, in some applications be the ambient magnetic field of the location in which the optical fibre is deployed. The ambient magnetic field may be the field resulting from the earth's magnetic field. The method may therefore rely on the earth's magnetic field interacting with the alternating current supplied to the conductor.

Tests have shown that the earth's magnetic field is strong enough to generate a detectable signal in an optical fibre coupled to a wire carrying an alternating current. In initial tests a current of the order of 3 A or so was sufficient to generate a signal in the presence of only the earth's magnetic field in a relatively noisy environment. In well adjusted embodiments however the current requirement may be lower, for instance currents of about 1 A or above would be sufficient and in some applications currents of the order of 10 mA or greater may lead to detectable measurement signals in the presence of the earth's magnetic field.

Where the earth's magnetic field is being used the general orientation of the magnetic field may be taken into account when deploying the optical fibre and conductor.

Figure 5:
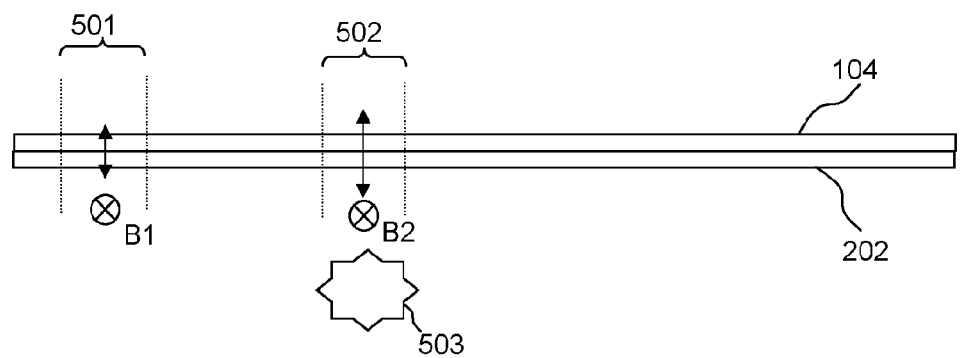
FIG. 5 illustrates magnetic field sensing according to an embodiment of the invention.

The method may also be used to determine the magnetic properties of the local environment as illustrated in FIG. 5 which shows a section of optical fibre 104 which is coupled to conductor 202. FIG. 5 illustrates two separated sensing portions 501 and 502 of optical fibre which may each generate a measurement signal.

Sensing portion 501 is in a part of the fibre which is located in an environment with a first magnetic property. In sensing portion 501 the only contribution to the local magnetic field may be the earth's magnetic field. Thus the magnetic field strength at sensing portion 501 may be a first level B1. Applying a defined AC current to conductor 202 would therefore generate a certain force on the conductor dependent on the magnetic field strength B1. This may lead to a first measurement signal. For ease the magnetic field is shown as into the plane of the paper but it will be understood that the field direction would depend on the location and the orientation of the optical fibre and conductor.

Sensing portion 502 is located in an area with a different magnetic characteristic. Sensing portion 502 runs close to object 503 which, in use generates a magnetic field. The object could be a permanent magnetic material or some other object that would produce its own magnetic field. For instance the object may be a power line which generates a magnetic field in operation due to the current flow within the power line.

Alternatively object 503 may be one which generates a secondary magnetic field in response the field generated in use by current flowing in the conductor 202.

In any case the object 503 thus contributes to the local ambient field strength B2 and thus may result in a magnetic field strength at sensing portion 502 which is significantly different to that (B1) experienced at sensing portion 501. Thus for the same applied AC current the force induced at sensing portion 502 may be significantly different to that induced at sensing portion 503. This may lead to a significant different measurement signal which may be used to determine the location of significant magnetic fields/anomalies in the environment.

This may be used for detecting objects that produce/interact with magnetic fields. It may also provide a method of structural monitoring of metallic items. An optical fibre and conductor could be deployed in the vicinity of a metallic object it is wished to monitor, for instance a railway track or a supporting beam in a structure. The structure may influence the magnetic fields in a certain way (for example due to magnetic domains formed within the structure). If the structural integrity of the item changes, for instance it develops a significant crack, this could affect its interaction with the magnetic field and thus result in a change in the ambient field strength. The resulting change in measurement signal may be detected and used as an indication of a problem. In addition to or instead of monitoring the magnetic properties of an individual item over time the method may also compare the results from different sensing portions adjacent different objects to detect any significant anomalies.

Note that the arrangement described above is suitable for detecting/monitoring relative magnetic field strengths of substantially constant magnetic fields. The method could also be used to detect varying magnetic fields. In fact if only varying magnetic fields are to be detected the current applied to conductor 202 could be a direct current. A varying magnetic field if present would then lead to a varying force on the conductor and hence optical fibre whereas any static or constant component of the magnetic field would lead to a DC offset in the measurement signal. Thus for instance if object 503 were a power cable carrying an AC current and hence produced a varying magnetic field, the power cable could be detected and/or monitored by applying a DC current to conductor 202.

Referring back to the idea of impedance sensing the current required to generate a detectable force may be reduced by deliberately increasing the magnetic field acting on the conductor. Therefore in some embodiments one or more elements may be deployed with the optical fibre and conductor to increase the magnetic field acting on the conductor, at least at some points along the length of the conductor.

Figure 6:
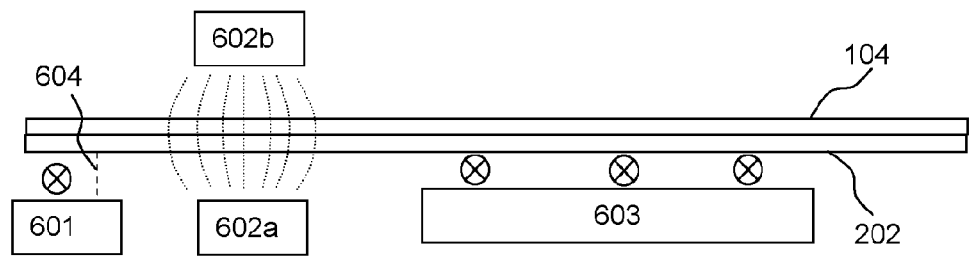
FIG. 6 illustrates an embodiment of the present invention with a magnetic element for creating a magnetic field on the conductor.

FIG. 6 shows one embodiment where a second element, comprising one or more magnetic elements, may be deployed in the vicinity of the optical fibre and conductor so as to increase the magnetic field (compared to the ambient field that would otherwise exist in the absence of the second element).

FIG. 6 shows that a permanent magnet 601 may be arranged in the environment in the vicinity of the optical fibre 104 and conductor 202. The permanent magnetic may be located relatively close to the optical fibre and conductor, for instance adjacent to a fibre optical cable structure, but may be separate therefrom. The permanent magnet 601 may be arranged so that the magnetic field it generates may have a desired orientation with respect to the optical fibre and conductor. Additionally or alternatively permanent magnets 602a and 602b could be located on either side of the optical fibre and conductor and their respective poles arranged to provide a desired field alignment. The permanent magnet may in some embodiments be an elongate permanent magnet 603 which is arranged to run alongside the path of the optical fibre and conductor so as to ensure that a significant portion of the optical fibre coupled to the conductor experiences a magnetic field above ambient strength.

Using permanent magnets may improve the detected measurement signal for a given AC current magnitude and/or reduce the current requirements. For instance in the presence of a magnetic field generated by a permanent magnet the current required to generate a detectable signal was significantly reduced, to the order of about 0.2 A in the tests referred to above.

A permanent magnet 601 may, in some embodiments, be connected to optical fibre 104 and/or first conductor 202 by a spring 604 or other similar elastic connection. The spring 604 will allow movement of the optical fibre 104 and conductor 202 relative to the magnet 601 but will ensure that the fibre at such point is particularly sensitive to certain frequencies and may provide a resonant frequency that varies according to the environment.

Figure 7:
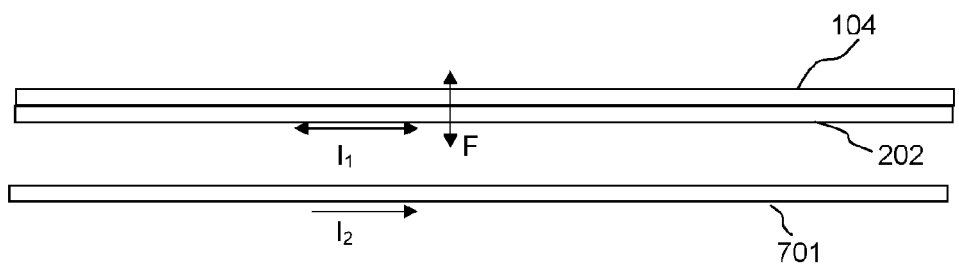
FIG. 7 illustrates a further embodiment with a magnetic element for creating a magnetic field on the conductor.

In addition to or instead of using permanent magnets a second conductor may be used to generate a magnetic field on the conductor coupled to the optical fibre. FIG. 7 shows an embodiment wherein a second conductor 701 is deployed in the vicinity of the optical fibre and first conductor. In use a first current $I_1$ current is supplied to the first conductor 202, coupled to optical fibre, and a second current $I_2$ is supplied to the second conductor 701. Both currents may be generated by driving circuit 204 or separate circuits may be used. As will be understood be one skilled in the art when two currents flow in parallel conductors a force will be developed on each conductor depending on the direction of current flow. As described previously, and as shown in FIG. 7 the current in the first conductor 202 may be an AC current whereas the current in the second conductor 701 may be a DC current. This will lead to a varying force F on the conductor 202 coupled to the optical fibre will varies between attraction and repulsion of the two conductors.

It will of course be appreciated that a similar effect could be achieved by generating a DC current in the first conductor 202 and an AC current in the second conductor 701.

In some embodiments both conductors may be supplied with AC.

In an alternative embodiment, referring back to FIG. 3, the conductor 202 may comprise a magnetostrictive material such as steel or nickel for instance. Magnetostrictive materials exhibit a change in dimensions in the presence of a magnetic field. When used as a conductor 202 the magnetic field generated in use by current flowing in the conductor may self-induce magnetostriction. As the current varies the degree of magnetostriction varies which results in a variable force on the conductor.

The embodiments described above have used a conductor coupled to the optical fibre. In an alternative embodiment a magnetic element may be coupled to the optical fibre and an alternating current applied so as to create a variable magnetic field thereby creating the stimulus on the optical fibre.

Figure 8:
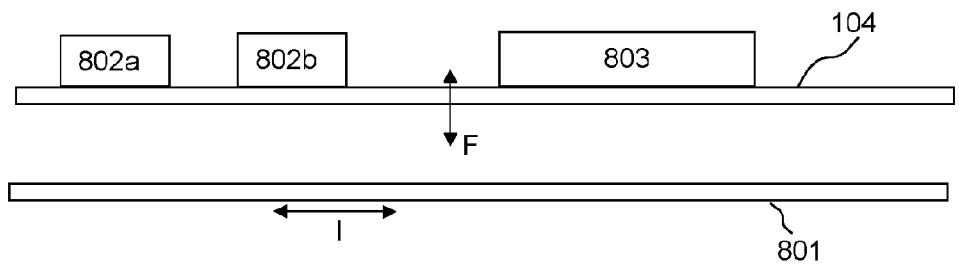
FIG. 8 illustrates an embodiment with magnetic material coupled to the optical fibre.

FIG. 8 illustrates an optical fibre 104 deployed in the vicinity of an elongate conductor 801, which may for instance be a conductive wire. The optical fibre may be attached to one or more magnetic elements 802a, 802b which are spaced along the length of the optical fibre and/or there may be an elongate magnetic element 803 coupled to a significant length of the optical fibre. The magnetic elements 802a, 802b or 803 may be permanent magnets or may be formed of paramagnetic or diamagnetic material.

In use an AC current is applied to the conductor 801 to generate a varying magnetic field so as to induce a varying force on the magnetic element(s) and thus the optical fibre 104.

Example 1

To demonstrate the principles of the present invention a 35 m length of fibre optic cable was bonded to a copper conductor. A frequency generator and amplifier were attached to the conductor to enable an electrical signal to be passed through the conductor. The fibre optic cable with bonded conductor was then orientated (magnetic) east-west on land, north-south on land and north-south in water for tests using the earth's magnetic field. The local angle of dip for the magnetic field was about 63°. A variety of current frequencies and amplitudes were fed into the conductor and the optical signal recorded. The current signal used was both continuous wave and frequency sweeps. When the fibre optic cable was in the north-south orientation recordings were made with the fibre optic cable lying on the surface of the ground, lightly covered in dry sand and with large pieces of ferrous metal in close proximity. Further tests were done using permanent magnets.

The results showed that a clear signal was visible at all current frequencies used when the current was above a few amps and the fibre optic cable was lying on the ground surface. The signal was greatly reduced when the fibre optic cable was covered in a thin layer of sand, or was submerged in water. Harmonics were visible in the detected signal and were dependent on the direction of the magnetic field with respect to the fibre optic cable. Thus analysing the harmonics may give information about the orientation of the magnetic field relative to the optical fibre.

Figure 9A:
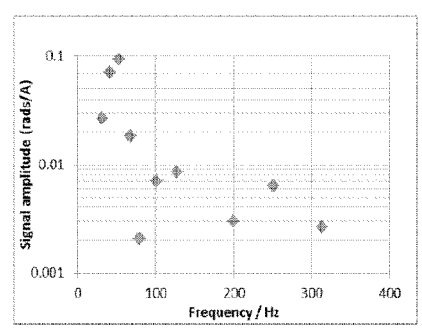
FIGS. 9a and 9b show results of the amplitude of measurement signal against frequency of the alternating current supplied.
Figure 9B:
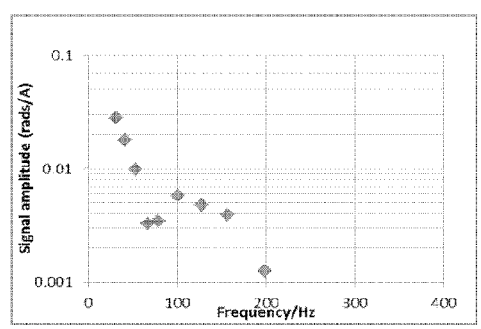

FIGS. 9a and 9b show some results indicating the amplitude of the measurement signal detected against frequency of the alternating current supplied. FIG. 9a shows the signal amplitude at a frequency corresponding to the fundamental amplitude and FIG. 9b shows the signal amplitude at twice the fundamental frequency. It can be seen that a measurement signal can be detected at a range of frequencies, up to at least 300 Hz, although the amplitude decreases with increasing frequency of the alternating current. The measurement signal may be expected to decrease with increasing frequency due to cable inertia. This suggests that an AC current with a frequency less than about 300 Hz may be useful. The results at lower frequencies are more noisy and thus a frequency above 1 Hz may be preferred. In use the frequency may be modulated to acquire readings at a number of different frequencies.

Example 2

To test that this measurement signal does indeed result from the interaction of the local magnetic field, i.e. the earth's magnetic field in the tests described above, a number of additional tests were performed in a laboratory setting.

Test 1—The measurement signal on the fibre was measured with an alternating current flowing through the copper conductor attached to the fibre optic cable and the Lorentz force was calculated assuming its origin to be due to the interaction of the current and the magnetic field of the earth.

Test 2—Permanent magnets were then used to increase the strength of the local magnetic field. The amplitude of the signal for a given AC electrical signal was found to increase with increasing magnetic field strength (resolved perpendicular to the axis of the fibre).

Test 3—The time varying current in the conductor attached to the fibre optic cable was then replaced with a steady current, and the DC magnetic field was augmented by an AC field generated from a large pair of Helmholtz coils. The strength of the varying force induced by this approach was calculated to be approximately the same as the varying force in test 1. The amplitude of the signal was also found to be approximately the same as in test 1.

Test 4—The copper wire was replaced by a nickel wire with known magnetostrictive properties. In this case the magnitude of the (much larger) signal was found to correspond with the amplitude expected by the magnetostriction of the nickel wire.

Example 3

Figure 10:
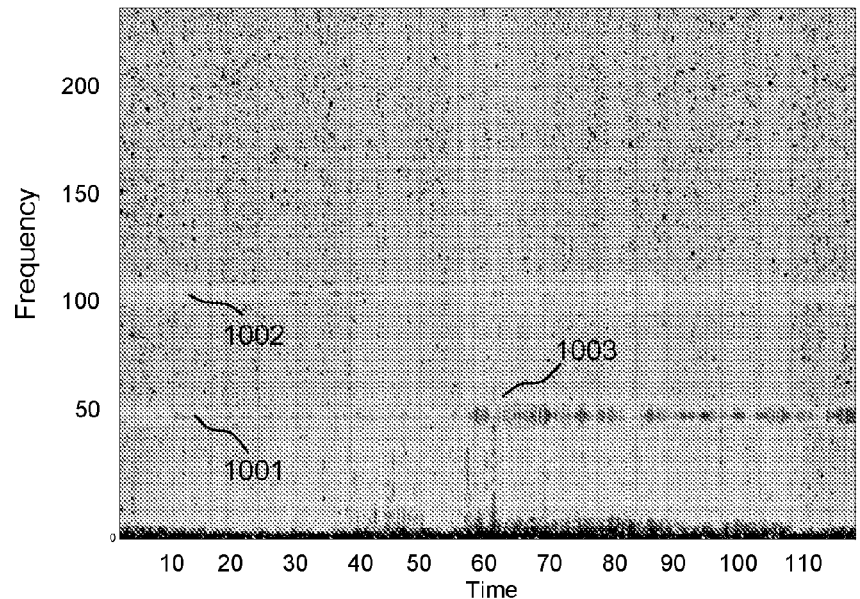
FIG. 10 shows a spectrogram of the measurement signal from a single sensing portion of optical fibre.

A clear change in the signal was also seen when large pieces of ferrous metal were placed near the fibre thus indicating the suitability for ferrous object detection. Using the same test set-up as Example 1 results were obtained over a period of 2 minutes while a 7 amp RMS alternating current was flowing in the conductor. For the first minute a 6 m long I-section mild steel beam was kept at a distance of 10 m from the fibre. Halfway through the period the beam was quietly lifted to within about 50 mm of the fibre optic cable. FIG. 10 shows a spectrogram for a single sensing portion of optical fibre at the location where the steel beam was introduced. FIG. 10 shows the variation in power distribution of the measurement signal in frequency against time. Intensity would normally be represented by colour.

It can be seen from FIG. 10 that there is a clear component 1001 of the measurement signal detected at about 53 Hz and also another 1002 at about 106 Hz. These signals (which are not as clear in the black and white version of FIG. 10 as the original plot) correspond to the fundamental frequency and first harmonic and are readily detectable in the measurement signal. Other, higher order harmonics can also be seen.

At 60 s, when the steel beam is brought into proximity the nature of the signals changes, especially the component around 53 Hz.

Figure 11A:
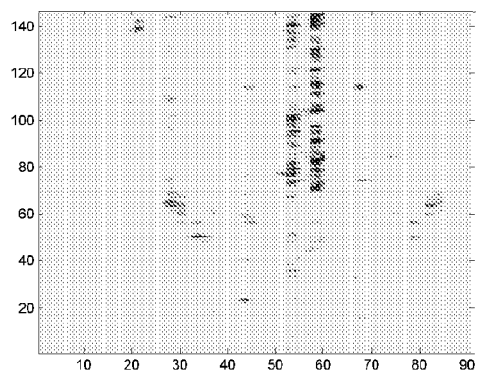
FIGS. 11a and 11b show power histograms in two frequency bands obtained in the presence of a metal beam.
Figure 11B:
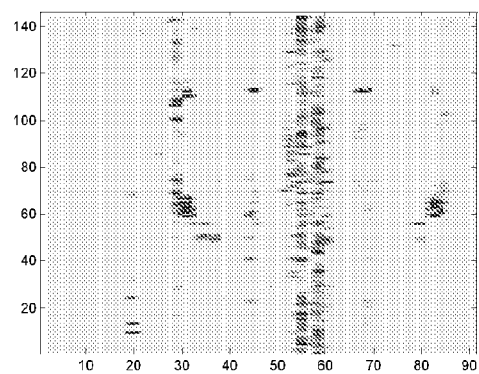

The measurements signals from a number of different sensing portions of the optical fibre were analysed further in two specific frequency bands as shown in FIGS. 11a and 11b. FIGS. 11a and 11b show the power in frequency band of 52 to 54 Hz and 104 to 108 Hz respectively, with time being plotted against optical channel (i.e. sensing portion) and power being represented by intensity. Optical channels 0 to 56 correspond to one optical fibre and optical channels 56 to 90 to a return path provided by another optical fibre in the same fibre optic cable. The copper conductor was bonded to the fibre optic cable corresponding to channels 53-56 in the outward path and 56-59 in the return path. The steel beam was located in the middle of the copper conductor and thus at a location corresponding to optical channels 54 and 58.

It can be clearly seen that the power corresponding to the fundamental frequency changes when the metal is brought into close proximity to the cable, but the amplitude of the first harmonic is fairly constant. This experiment was repeated at a range of frequencies with similar results.

This indicates that the presence of ferromagnetic material can be detected from the measurement signal acquired when applying a varying current.

These tests and examples show the application of the present invention to detection of the characteristic of the environment such as impendence or magnetic properties. This environmental sensing may be performed as the principal aim of the sensor but in some embodiments the apparatus may be used for some other fibre optic sensing. For instance referring to FIG. 2 interrogator 201 may be arranged to interrogate the optical fibre 104 to provide a distributed acoustic sensor. The interrogator may principally operate as a DAS sensor without a current flowing in the conductor so to detect acoustic signals from the environment. Periodically however the sensor may be arranged to acquire apply the AC current to the conductor 202 so as to determine the characteristics of the environment.

Whilst interrogator 201 may provide DAS sensing when the AC current is not applied in other embodiments the interrogator may provide other sensing functionality, for instance DTS. In some applications the measurement signals acquired when the AC current is applied may be used to calibrate the signals from the sensing portions in the absence of the AC current.

In one embodiment, instead of detecting an inherent property of the environment, a variable impedance may be used to provide an additional sensing capability. The fibre optic cable may be coupled to, or embedded within a material whose impedance properties, viscosity, deformability, stiffness etc. vary with a desired parameter it is wished to sense. The method may therefore comprise determining the impedance of the material and hence the sensed parameter.

For instance referring back to FIG. 4c the intermediate material 408 could be a gel whose viscosity varies with temperature or UV exposure (through a uv transparent jacket 407) or could comprise a crushable material that deforms with pressure. In any of these cases the impedance to movement of the optical fibre within the cable is determined by the parameter it is desired to sense (provided the outer cable is relatively fixed in the environment).

The invention claimed is:

1. A method of fibre optic sensing comprising:
   interrogating an optical fibre deployed in an area of interest with optical radiation wherein at least part of the optical fibre is mechanically coupled to at least a first element responsive, in use, to electromagnetic fields;
   applying a varying electric current so as to induce a varying force on said first element; and
   analysing optical radiation backscattered from within said optical fibre to determine a measurement signal indicative of a variation in the backscattered radiation corresponding with said electric current applied;
   analysing said measurement signal to determine a characteristic of the environment in which the optical fibre is deployed; and
   determining the mechanical impedance of the environment.

2. A method as claimed in claim 1 wherein the first element is a first conductor.

3. A method as claimed in claim 2 comprising generating, in use, a current in the first conductor in the presence of a magnetic field wherein the varying current is applied so as to create varying current flow in the first conductor and/or a varying magnetic field.

4. A method as claimed in claim 3 comprising arranging the optical fibre and first conductor in a magnetic field in use, wherein the varying current is applied to the first conductor to induce the varying force on the first conductor.

5. A method as claimed in claim 4 wherein substantially the main component of said magnetic field is the magnetic field of the earth.

6. A method as claimed in claim 4 comprising arranging at least a second element that, in use, generates a magnetic field in the vicinity of the first element.

7. A method as claimed in claim 6 wherein the second element forms part of a fibre optic cable structure with the optical fibre and first conductor, the structure being configured to allow at least some motion of the first conductor relative to the second element.

8. A method as claimed in claim 6 wherein the second element comprises a permanent magnetic material.

9. A method as claimed in claim 6 wherein the second element comprises a second conductor.

10. A method as claimed in claim 2 wherein the first conductor comprises a conductive wire, which runs along the length of at least part of the optical fibre.

11. A method as claimed in claim 2 wherein the first conductor at least partly surrounds the optical fibre.

12. A method as claimed in claim 1 wherein the first element comprises at least one magnetic element responsive to an applied magnetic field and the method comprises applying the varying current so as to vary the magnetic field acting on the first element.

13. A method as claimed in claim 1 wherein the method comprises a method of structural monitoring.

14. A method as claimed in claim 1 wherein determining the characteristic of the environment comprises comparing different measurement signals from different parts of the optical fibre, and/or measurement signals from a given section of the optical fibre acquired at different times, to give a relative measure of the characteristic of the environment.

15. A method as claimed in claim 1 further comprising interrogating the optical fibre without the varying current being applied to provide at least a first sensing function, wherein the first sensing function comprises distributed acoustic sensing or distributed temperature sensing.

16. A method as claimed in claim 15 wherein the determination of the environmental characteristic is used to calibrate for the measurements of the first sensing function.

17. A method as claimed in claim 1 wherein the varying current applied is an alternating current.

18. A method as claimed in claim 17 comprising varying at least one of the frequency and/or magnitude of the alternating current applied.

19. A method as claimed in claim 1 wherein the optical fibre and first element are coupled to a material whose properties vary in accordance with a first parameter to modify the environmental characteristics of the optical fibre.

20. A method as claimed in claim 19 wherein the first parameter is one of, temperature, humidity, uv radiation, ionising radiation, concentration of target chemical species or pressure.

21. A method as claimed in claim 19 comprising determining the impedance of the environment and using the impedance as an indication of the first parameter.

22. A fibre optic sensor apparatus comprising:
   an optical fibre, at least part of which is mechanically coupled to at least a first element responsive, in use, to electromagnetic fields;
   an interrogator unit for interrogating said optical fibre with optical radiation;
   an electrical circuit for generating a varying electric current so as to induce a varying force on said first element; and
   a processor configured to analyse optical radiation backscattered from within said optical fibre to determine a measurement signal indicative of a variation in the backscattered radiation corresponding with said electric current applied and analyses said measurement signal to determine a characteristic of the environment in which the optical fibre is deployed, the processor further configured to determine a mechanical impedance of the environment.

* * * * *